United States Patent [19]
Wilson, Jr. et al.

[11] Patent Number: 5,336,090
[45] Date of Patent: Aug. 9, 1994

[54] TRANSMUCOSAL HEALING CAP AND LOCKWASHER FOR DENTAL IMPLANTS

[76] Inventors: Richard S. Wilson, Jr., 1416 Burmont Rd., Havertown, Pa. 19803; Barry Sukoneck, 935 Remington Rd., Wynnewood, Pa. 19096; Kenneth C. Wenzer, 11538 February Cr. #402, Silver Spring, Md. 20904

[21] Appl. No.: 159,326

[22] Filed: Nov. 30, 1993

[51] Int. Cl.$^5$ .................. A61C 8/00; A61C 13/12; A61C 13/225
[52] U.S. Cl. ................ 433/172; 433/173; 433/177
[58] Field of Search ............ 433/172, 173, 174, 175, 433/176, 177

[56] References Cited

U.S. PATENT DOCUMENTS

| | | | |
|---|---|---|---|
| 4,856,994 | 8/1989 | Lazzara et al. | 433/173 |
| 4,872,840 | 10/1989 | Bori | 433/173 |
| 5,006,069 | 4/1991 | Lazzara et al. | 433/173 |
| 5,030,096 | 7/1991 | Hurson et al. | 433/173 |
| 5,035,619 | 7/1991 | Daffary | 433/173 |
| 5,049,073 | 9/1991 | Lauks | 433/173 |
| 5,154,612 | 10/1992 | Carlsson et al. | 433/173 |

Primary Examiner—Robert P. Swiatek
Assistant Examiner—Nicholas D. Lucchesi
Attorney, Agent, or Firm—Robert Halper

[57] ABSTRACT

Specially designed healing caps with varied bottom surfaces and different shaped channels and diverse shaped lockwashers for obviating loosening of the healing cap when screwed into an implant fixture. The healing cap has a retaining screw separate from the cap body and the combination of healing cap and lockwasher also prevents breakage of the cap body or fixture or both due to excessive torque and prevents gingiva from growing over the fixture at any point.

8 Claims, 5 Drawing Sheets

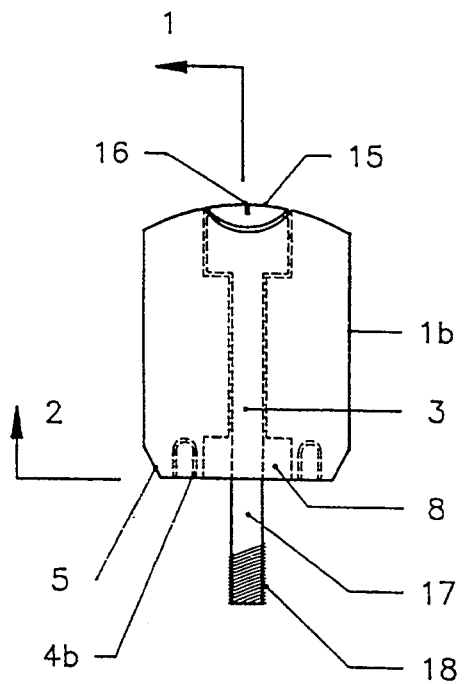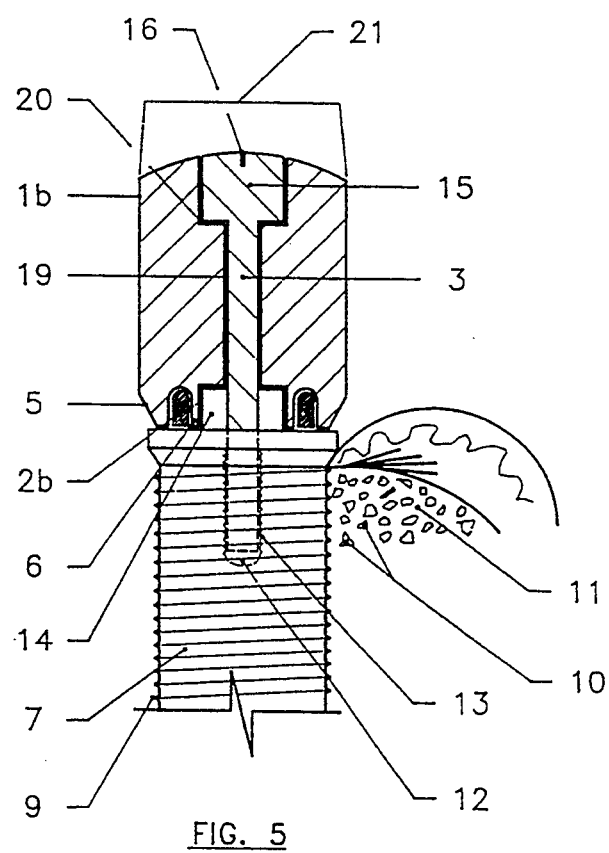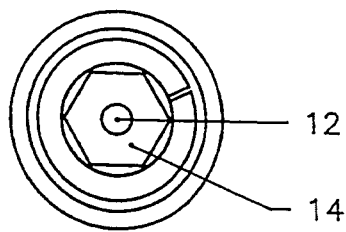

TRANSMUCOSAL HEALING CAP AND LOCKWASHER FOR DENTAL IMPLANTS

FIELD OF THE INVENTION

This invention concerns a lockwasher and a transmucosal healing cap for dental implants. The main goal of the invention is the improved seating and fixing into place of the healing cap placed in the interval between surgery and abutment selection/prosthesis fabrication, thus preventing scaling of the sulcus on the fixture and undesirable tissue entrapment developing between the fixture and abutment. A secondary goal is to avoid damage to the fixture as a result of excessive torque.

BACKGROUND OF THE INVENTION

Current examples of healing caps are exemplified by U.S. Pat. Nos. 4,856,994, 5,006,069, 5,030,096, 5,035,619, and 5,154,612. 4,856,994 shows an implant installed in a jaw bone. The implant has an internally threaded bore that opens to the gum and an hexagonal fitting placed on top of the implant. An opening in the gum is preserved by use of a healing cap having an upper convex surface. The cap is intended to be flush or slightly outside the outer surface of the surrounding gum. The underside of the cap is reentrantly shaped to provide a cavity surrounded by an annular skirt terminating in an annular meeting surface. The cap is installed on the implant by threading a post into the threaded base of the implant until the annular meeting surface is in contact with the top surface of the implant. The novelty of this invention is to shield the upper surface of the implant from overgrowth of gum tissue and at the same time maintaining an opening through the gum tissue that overlies the implant. An additional feature is the use of a manipulating tool that fits into the cap and enables it to be fixed and located in place. U.S. Pat. No. 5,006,069 pertains to fixing a temporary restoration to an underlying implant. A dental coping is in the form of an elongated tubular body and has a base portion that is adapted to the first end of the body to mate with a support in the form of an integrated tapered post component that has a transmucosal section and a conical supragingivally extending male post section. A thin walled portion of the body extends upwardly from the base portion and has a seat for a bolt that fixes the tubular body and tapered post to the implant. The coping is intended for removably fixing a temporary restoration on the support. U.S. Pat. No. 5,030,096 has to do with an implant healing cap and holder. The invention enables a surgeon to handle an implant within the patient's mouth more readily. A threaded screw cap fits into a biocompatible implant. The cap screw has a head about the diameter of the end of the implant to protect the same. There is a cavity in the head of the cap for insertion of a wrench. A holder has a projection that fits resiliently into the cavity of the screw cap. After the installation of the implant with a screw cap by gripping the holder, positioning the implant and pushing it into place, the holder can be simply removed by bending the holder to one side and removing the holding projection from the cavity. U.S. Pat. No. 5,035,619 teaches a dental implant that has improved resistance to infection and a healing cap that does not need to be removed upon installation of a temporary or permanent crown. The invention uses a cover screw for sealing the hollow portion of the implant fixture during the time the jaw bone is growing about the fixture. After osseointegration of the fixture, the gingiva is reopened, the cover screw removed and replaced by a transmucosal healing cap. The healing cap is configured to allow the gingival tissues that were surgically displaced during removal of the cover screw to heal around the cap in a shape that is dimensionally similar to the previously removed tooth. The healing cap is made in two parts, one part being of frustoconical shape and having a stem attached to its proximal end and a cylindrical part above the frustoconical part that has a screw head segment for insertion of a driving tool. The fixture has a raised lip at its upper surface which may be circular or hexagonal. The lip fits within an approximately configured socket of the healing cap and its engagement within the socket provides additional support to the securing of the healing cap to the fixture. Several other types of healing caps are shown. After healing, the cap is removed and replaced by an abutment having an emergence profile matching that of the healing cap. U.S. Pat. No. 5,154,612 shows a device which includes a dental implant having a titanium screw and a spacer element arranged between two natural teeth. A crown between two natural teeth is applied on the spacer by means of cement. Prior to placement of the crown a cap is temporarily arranged on the spacer during which period the gum swelling will subside. The base part of the cap is wider than the base part of the spacer in order to hold the gum away from the shoulder of the spacer element and a pocket can be formed in the gum that is slightly larger than the crown. The base part of the cap extends some distance down into the edge of the gum.

The patents cited above show the state of the art. To recapitulate, the dental implant is generally performed by an oral surgeon. After a healing period of 3-6 months, the implant is exposed. A general dentist or prosthodontist then performs the restoration, which involves placement of an abutment of a specific size and shape over the fixture and securing the same by means of a bolt threaded into a cavity in the fixture. The implant fixture distal surface contains a flat, polished outer ledge and a central hex which is then engaged by a tool during placement. Also indicated by the prior art is a submucosal healing cap and a transmucosal healing cap to prevent the anatomy from becoming infiltrated with tissue from the gingiva and/or bone. The removal of such tissue is difficult and causes scratching of the abutment. In addition to keeping tissue out of the fixture the healing cap establishes a sulcus or opening above the fixture to allow placement of an abutment. The sulcus formed by the healing cap must be of sufficient size so that the various permanent abutments fit comfortably without causing tissue tearing and bleeding.

While these aforementioned healing caps have done a credible job in preventing tissue infiltration and establishing the necessary profiling for abutment attachment and placement of a tooth analogue, they suffer from a common defect in that while they screw into place using the fixture's internal threaded channel, they tend to loosen in a high percentage of cases, regardless of the torque used to tighten them. The result is tissue infiltration over the distal surface of the fixture. Removal of this tissue must be attempted under local anaesthetic. Such removal is difficult, uncertain, painful and likely to cause highly undesirable scratching of the highly polished surface of the fixture. Furthermore, because of the excessive torque sometimes used to tighten the healing cap on the fixture, breakage of the fixture and/or the healing cap can occur. Finally the high torque used to loosen the healing cap may loosen the fixture as well, causing damage to the osseointegration between the bone and fixture. Thus there exists a need for a healing cap that can obviate the above mentioned difficulties.

It is an object of this invention to design a healing cap and lockwasher that will not loosen and thus avoid tissue infiltration on the surface of the fixture.

It is a further object of the invention to prevent the need for removal of tissue that infiltrates the distal surface of the fixture.

It is still an object of this invention to design a healing cap that will avoid the use of excessive force when affixing to the implant so as to prevent damage to the fixture or healing cap or both.

SUMMARY OF THE INVENTION

The invention provides a healing cap that does not loosen and does not require the use of excessive torque that might damage the fixture or the healing cap or both. This effect is accomplished by the use of two components, a specially designed healing cap and a specially designed lockwasher.

The healing cap consists of a body and a retaining screw. The healing cap body is made with several variations. One contains channels on its lower surface that engage both a hexagonal fitting on the upper surface of the implant and a lockwasher. In a second variation the healing cap is open towards the center at its lower surface and in a third variation there are no channels at its lower surface.

The lockwasher is a helical segment made of a precious element such as Type II casting gold alloy or pure titanium. Viewed from above it is circular in shape with a break in the circle. The break is at a 60 degree angle from the horizontal as viewed from the side. When compressed, the lockwasher flattens into a ring and the helical shape is completely lost.

BRIEF DESCRIPTION OF THE DRAWINGS

FIG. 4 is a frontal view showing a first modification of the healing cap of FIG. 1.

FIG. 5 is a sectional view taken on line 4—4 of FIG. 4 and includes an implant assembly.

FIG. 6 is a plan view taken on line 6—6 of FIG. 4.

DETAILED DESCRIPTION OF THE INVENTION

Figure 1:
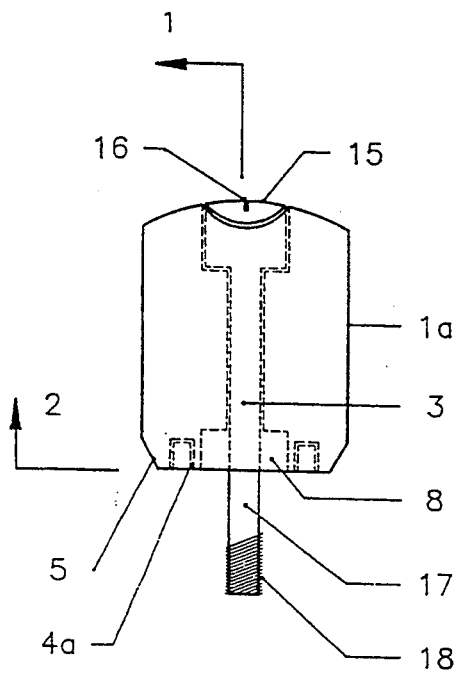
FIG. 1 is a frontal view of the healing cap.
Figure 2:
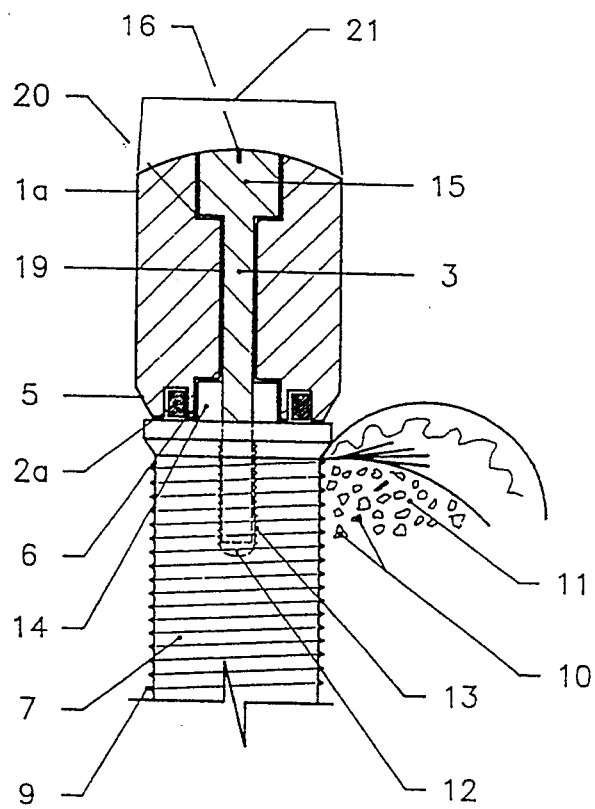
FIG. 2 is a sectional view taken on line 1—1 of FIG. 1 and includes an implant assembly.
Figure 3:
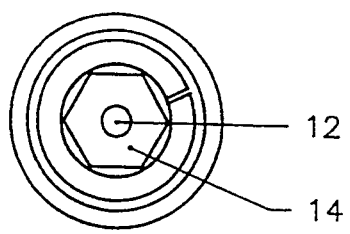
FIG. 3 is a plan view taken on line 2—2 of FIG. 1.
Figure 7:
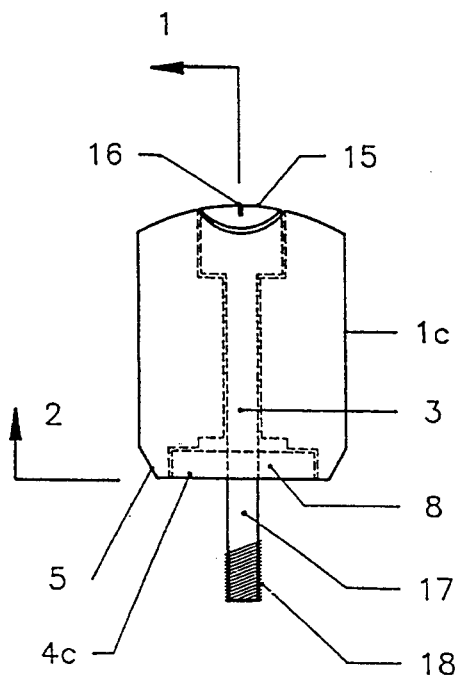
FIG. 7 is a frontal view showing a second modification of the healing cap.
Figure 8:
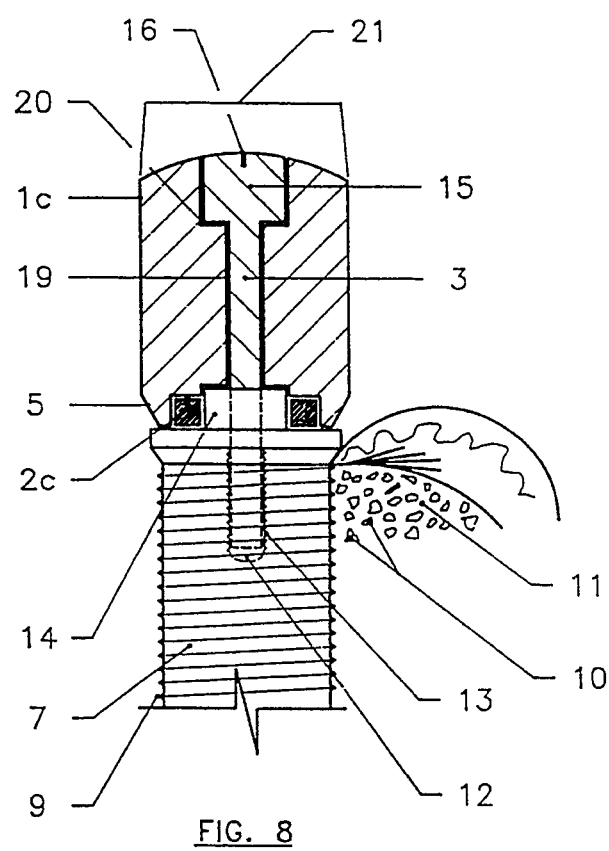
FIG. 8 is a sectional view taken on line 7—7 of FIG. 7 and includes an implant assembly.
Figure 9:
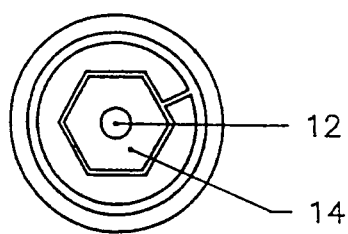
FIG. 9 is a plan view taken on line 9—9 of FIG. 7.
Figure 10:
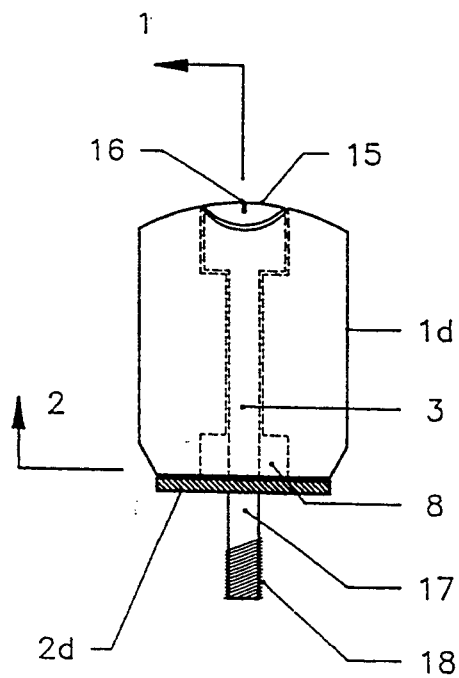
FIG. 10 is a frontal view of a third modification of the healing cap of FIG. 1.
Figure 11:
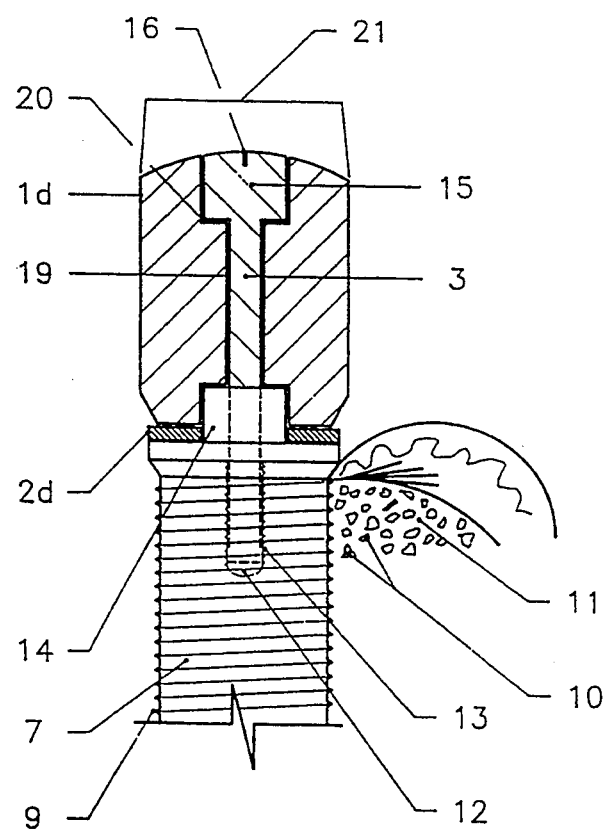
FIG. 11 is a sectional view of FIG. 10 taken on line 10—10 and includes an implant assembly.
Figure 12:
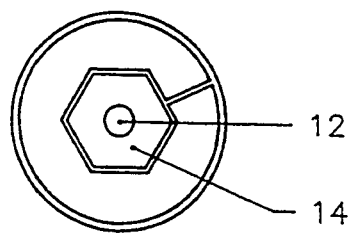
FIG. 12 is a plan view taken on line 12—12 of FIG. 9.
Figure 13:
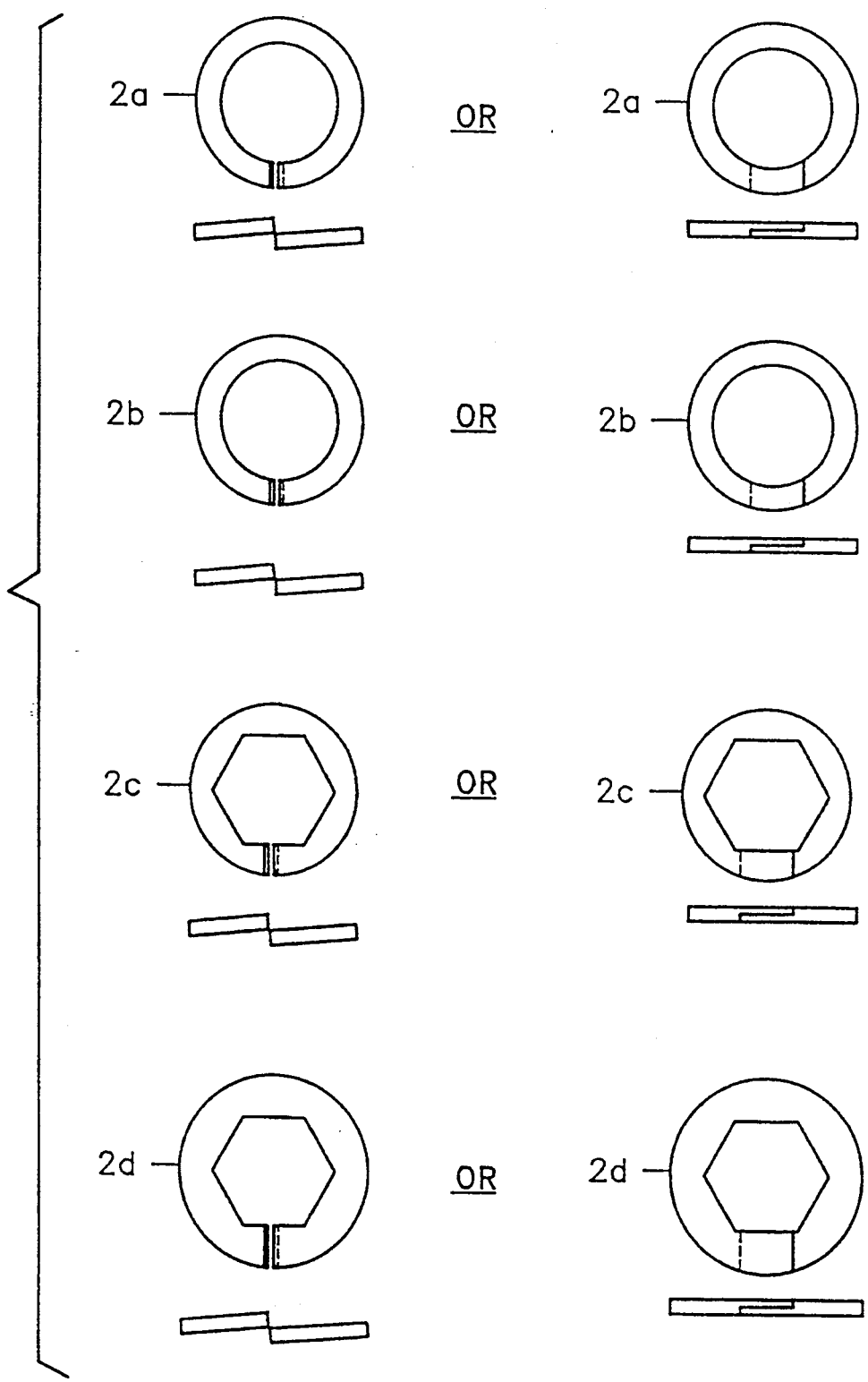
FIG. 13 is a view showing details of the different lock washers per se.

The device as seen in FIGS. 1 and 2 consists of a special healing cap body 1a, a helical lockwasher 2a and a separate retaining screw 3. The lockwasher is helical in shape and as seen from above is in the form of a split ring, the split being at an angle of 60 degrees from the horizontal. As seen in FIGS. 4 and 5 lockwasher 2b can also be made with a different shape. Instead of being flat on its top surface, it can also be made semicircular. The internal diameter of lockwashers 2a and 2b are both circular in shape. The proximal surface of the body 1a, 1b includes two concentric raised platforms 5 and 6 that define a lockwasher channel 4a, 4b. If the lockwasher 2b is used, then channel 4b having a semicircular shape will be made to conform to the shape of the washer. An additional purpose of the platforms is to bear on an implant fixture 7. The lockwasher fits neatly in the lockwasher channel and provides mechanical retention. By virtue of the securement of the lockwasher in its channel, the healing cap can be readily placed on the fixture. In these two aforementioned embodiments the lockwasher channel is 1.50 mm in depth, so that when the lockwasher is fully compressed, it is flush with the raised platforms and at the same time the raised platforms will bear forcefully on the distal surface of the fixture. Thus the outer platform 5 prevents gingival tissue from proliferating into the fixture. A further feature of the cap body is a hexagonal channel 8 that extends upwardly from the inner platform 6 and has a vertical axis coincident with the central vertical axis of the cap body. The implant fixture 7 is of conventional construction and has a threaded outer surface 9 that threadingly engages a previously drilled and threaded surface of the jawbone 11. In the center of the fixture is a cavity that has a threaded surface 13. On the distal surface of the fixture and around the cavity is a hexagonal fitting 14. When the healing cap is mounted on the fixture this fitting will fit into the hexagonal channel 8. There is a slight clearance to allow for rotation of the cap body. FIGS. 7 and 8 shows a third modification of the healing cap 1c. In this modification platform 6 is eliminated and the inner diameter of the lockwasher 2c would be hexagonal which would precisely engage the hexagonal fitting on the fixture while its outer diameter would fit within platform 5. There would still be clearance between the hexagonal fitting and the hexagonal channel to allow rotation. The advantage of this variation is that it would allow the lockwasher to be thicker and stronger. Lockwasher retention would still be provided through friction and a close fit between the outer circumference of the washer and the raised platform. A fourth variation as shown in FIGS. 10 and 11 eliminates both platforms. In this case the lockwasher 2d would have approximately the same diameter as the healing cap 1d and the distal surface of the fixture. In this case lockwasher 2d need be only 0.75 mm in height. This allows hexagonal fitting 14 to protrude slightly (0.25 mm) above the lockwasher. Again the advantage is lockwasher size which provides not only greater strength but also ease of manipulation. One disadvantage, however, is that lockwasher 2d cannot be carried into position by the healing cap since there is not mechanical retention. In this case the internal circumference of washer 2d would be configured to precisely fit the hexagonal fitting on the implant. This design does allow placement of the lockwasher on the implant fixture. Once this placement is complete the healing cap body can be placed into position over the lockwasher and tightened with the retaining screw. This action would compress the lockwasher into its final flat shape. The retaining screw comprises a head 15 with a groove 16 on its top to allow for the manipulation of a screwdriver, shaft 17 and a threaded section 18 on the end of the shaft that extends past the cap body. On the distal surface of the cap body there is formed a channel 19 having a vertical axis coincident with the central vertical axis of the cap body. At the bottom of the channel is a seat 20. This structure precisely fits the retaining screw head and its horizontal plane provides a force bearing structure, so that when tightened the retaining screw secures the healing cap body and lockwasher against the fixture, compressing the lockwasher in the process and securing the entire assembly against loosening. The distal surface 21 of the cap body would be slightly convex as would be the head of the retaining screw. FIG. 13 shows other details of the lockwashers. Before assembly the lockwasher is in the shape of a helix and the ring can be made such that the ends of the split can be in the form of two angular members with the longer legs of each member overlapping each other rather than the 60° split between the two ends as described above.

The concept of combining a two piece component (body and retaining screw) and a lockwasher can be applied to other aspects of the implant system as well, for example, the abutment and/or the prosthesis. A modified proximal surface of one of the various existing abutment designs with the lockwasher design as described above placed between an abutment and a fixture would prevent inadvertent loosening of the abutment. A modified proximal surface of the prosthesis and a lockwasher fitting the existing distal surface of the various existing abutment designs would prevent inadvertent loosening of the prosthesis. Finally the various temporary screws which correspond to the specific abutment types may also benefit from a lockwasher mechanism.

In practice, the procedure would be as follows. When the fixture is exposed during a second surgery, the clinician obtains a flap and dry field in the usual manner. The lockwasher is placed at the proximal surface of the healing cap and over the fixture and its hexagonal fitting and is manually stabilized. The retaining screw is then tightened until the lockwasher compresses fully. The transmucosal healing cap assembly is now tightly adapted to the fixture. Inadvertent loosening of the healing cap will not occur, thus preventing tissue from invading the sulcus and fixture. When desired, e.g., when placing the abutment of choice, the healing cap can be readily removed with a screwdriver.

While the invention has been described in considerable detail, it should not be considered as restricted to such detail, as many modifications of the healing cap and lockwasher are conceivable without departing from the spirit and scope of the appended claims.

We claim:

1. A specially designed healing cap and implantable fixture, said cap having a centrally located cavity, comprising:

a cap body having a vertical axis that extends through the center of said cavity, a distal surface and a proximal surface, a first circular channel extending inwardly from said distal surface to said cavity said channel having a vertical axis coincident with said axis of the cap body and a seat at the juncture of said channel and said cavity, a second hexagonal channel extending inwardly from said proximal surface and in alignment with said first channel;

said implantable fixture further having a distal surface and a proximal surface, said fixture directly underlying the proximal surface of said cap body, and having a hexagonal fitting on its distal surface, in alignment with and nestled in said hexagonal channel, said fixture having a threaded opening and a vertical axis coincident with the axis of said cavity;

a retaining screw having a grooved head that fits precisely in said seat and a shaft having a threaded end section that extends through said cavity and said hexagonal fitting and screws into said threaded opening in said fixture;

a helical washer between said proximal surface of said healing cap and said distal surface of said fixture and around said hexagonal channel, said helical washer being in the form of a split ring having ends that are inclined from the horizontal, said washer assuming the shape of a flat ring when compressed by turning of said retaining screw so as to join said healing cap and fixture in a tight fit.

2. The healing cap of claim 1 wherein outwardly adjacent said hexagonal channel and at the proximal surface of said cap body is a lockwasher channel being defined by an inner and outer raised platform, said helical washer having a circular inner circumference and being retained in said channel such that when fully compressed is flush with said raised platforms, said platforms bearing forcefully on the distal surface of said fixture.

3. The healing cap of claim 1 wherein said hexagonal channel is located above said proximal surface of said cap and a lockwasher channel is proximal outwardly adjacent said hexagonal channel and at said proximal surface of said cap body, said lockwasher channel being defined by a single raised platform, said helical washer fitting in said lockwasher channel and having a hexagonal inner circumference that precisely engages said hexagonal fitting, said helical washer having a sufficient thickness and strength to fully occupy said lockwasher channel.

4. The healing cap of claim 1 wherein said cap body has an outside surface and wherein said proximal surface of said healing cap body is flat and said helical washer extends from said hexagonal fitting to the outside surface of said healing cap body.

5. The healing cap of claim 4 wherein the internal diameter of said helical washer is hexagonal in shape.

6. The healing cap of claim 1 wherein there is a slight clearance between said hexagonal channel and said hexagonal fitting so as to allow for rotation of said healing cap.

7. The healing cap of claim 1 wherein said helical washer is made of titanium, said helical washer is 1.5 mm in depth and the angle of inclination of said ends is 60°.

8. The healing cap of claim 1 wherein said helical washer is made of Type II casting gold alloy and the angle of inclination of said ends is 60°.

* * * * *